United States Patent [19]

Caspari et al.

[11] Patent Number: 4,457,302
[45] Date of Patent: Jul. 3, 1984

[54] LEG IMMOBILIZING APPARATUS FOR ARTHROSCOPIC SURGERY

[75] Inventors: Richard B. Caspari, Maidens; Terry L. Whipple and James A. Thimsen, both of Richmond, all of Va.

[73] Assignee: Precision Surgical Instruments, Inc., Richmond, Va.

[21] Appl. No.: 439,439

[22] Filed: Nov. 5, 1982

[51] Int. Cl.$^3$ ............................................. A61F 13/00
[52] U.S. Cl. .................................... 128/133; 269/328
[58] Field of Search ............... 128/133, DIG. 20, 134, 128/DIG. 15, 327; 269/328, 322

[56] References Cited

U.S. PATENT DOCUMENTS

| | | | |
|---|---|---|---|
| 4,045,678 | 8/1977 | Rickard | 269/328 |
| 4,232,681 | 11/1980 | Tulaszewski | 128/133 |
| 4,299,213 | 11/1981 | Violet | 128/133 |
| 4,373,709 | 2/1983 | Whitt | 128/133 |

Primary Examiner—John D. Yasko
Attorney, Agent, or Firm—Richard P. Matthews

[57] ABSTRACT

A leg immobilizing apparatus especially useful in connection with arthroscopic knee surgery wherein the surgeon views the knee on a television screen. A flat bar member is extended across an operating table and is secured to horizontally extending rail members customarily provided on operating tables. Depending clamps from the bar member are releasably secured to the rail members. The patient's leg which is to be operated upon is cradled by a pair of plates carried by the bar member and angularly disposed thereto. A specially designed sphygmomanometer constitutes a tourniquet member and applies a known pressure to the thigh of the patient. The design permits the tourniquet member to be secured to the leg cradling apparatus. A strap resembling an automobile safety belt is anchored to the leg cradling apparatus and provides a supplementary leg holder. The patient is customarily electrically grounded and the apparatus is provided with an electrically insulating coating.

22 Claims, 10 Drawing Figures

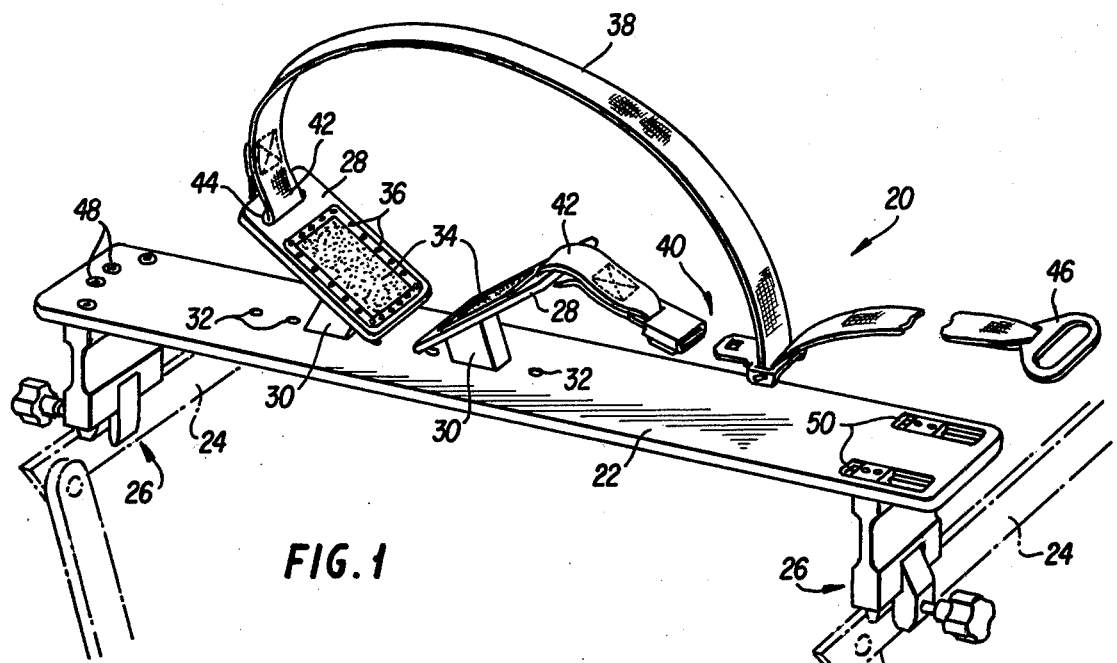
FIG. 1
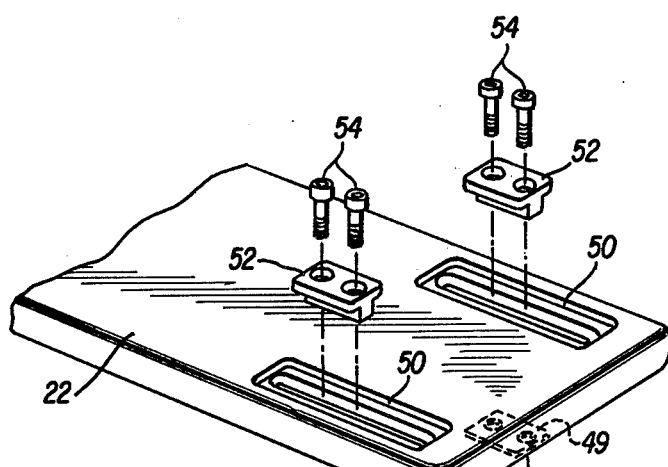
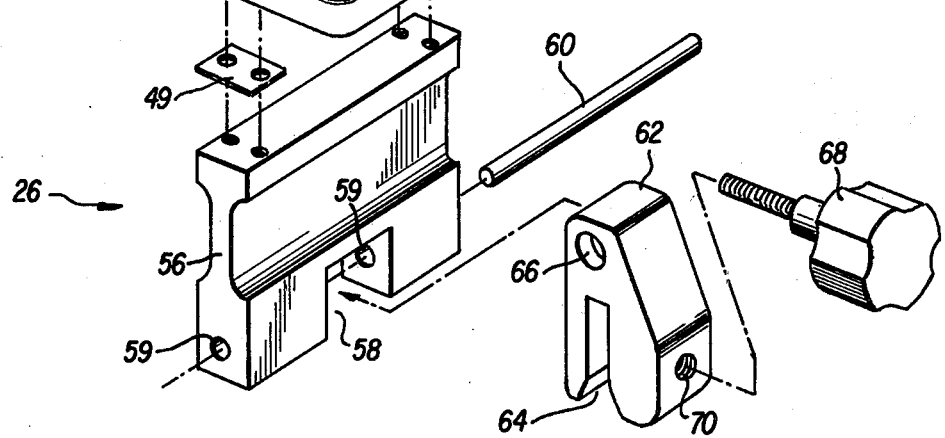
FIG. 2

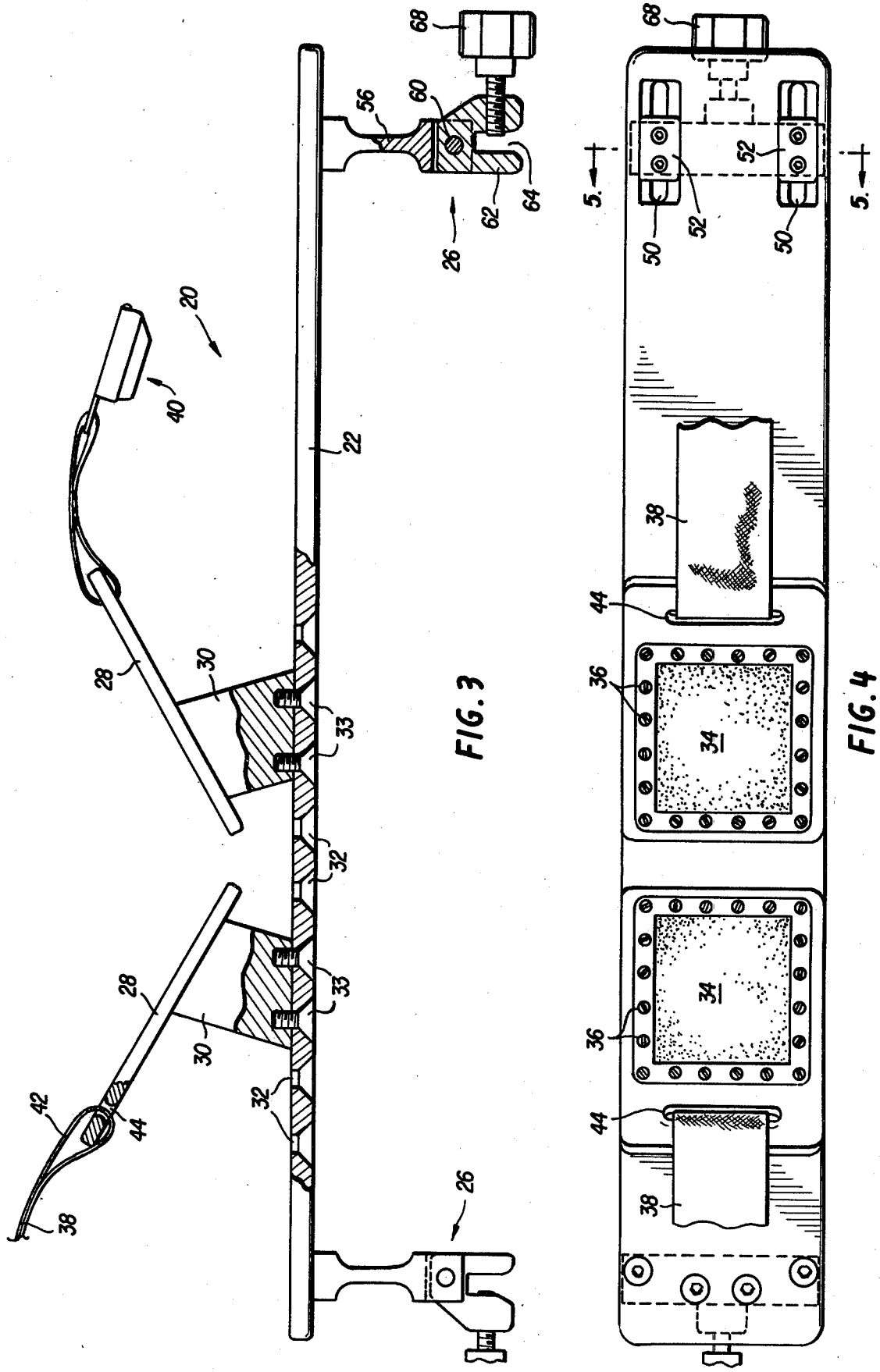

LEG IMMOBILIZING APPARATUS FOR ARTHROSCOPIC SURGERY

This invention relates to a leg immobilizing apparatus and, more particularly, to such an apparatus especially useful in connection with arthroscopic knee surgery.

BACKGROUND OF THE INVENTION

Arthroscopic surgery is being used much more frequently in knee surgery and in the diagnosis of knee injuries. An arthroscope resembles a long, very narrow tube and may be provided with a magnifying lens at one end. The arthroscope is inserted through a very small puncture wound of the knee, in the order of from 2-5 millimeters in diameter rather than a relatively large incision. The surgeon examines the knee through the arthroscope and inserts small instruments through other puncture sites. In the preferred arthroscope models used in the present invention the viewing area of the arthroscope is magnified and projected onto a television screen whereby the surgeon actually performs the surgery while viewing the television screen.

Because a substantially smaller puncture-type wound is made in the knee, the surgery may be performed under a local anesthetic and the operation may be completed in approximately twenty minutes as compared with from one and one half to two hours previously. Since the damage to the knee is so much less from the small puncture wounds, the patient's recovery time is substantially less. The patient customarily is up and walking within one day and in some instances even sooner.

It has been the practice in the past to use a post which did not permit any rotational control and a strap to hold the patient's leg immobile while the operation was being performed. Tourniquets were placed on the leg, but the amount of pressure applied has not been known. Moreover, it has been necessary to break the sterile field when other procedures, such as taking X-rays or the like, were required.

SUMMARY OF THE INVENTION

In accordance with the present invention the foregoing limitations and shortcomings of the known prior art are effectively overcome. In particular, the leg immobilizing apparatus of the present invention provides a bar which extends completely across the operating table and is adjustably clamped to a pair of horizontally extending parallel rails customarily provided on operating tables. The bar carries plate members which are angularly disposed with respect to the bar so as to provide a cradling means for the leg of the patient. A tourniquet means in the form of a specially designed sphygmomanometer applies a known pressure to the thigh of the patient. The tourniquet means is releasably attached to the angularly disposed plate members carried on the bar. A supplementary leg holder is provided by a strap which resembles an automobile safety belt and which is anchored to the plate members. Because electricity is used in the operating region to magnify and display the viewing area on a television screen and because water is used to irrigate the knee during the operation, it is customary to ground the patient electrically and to provide an electrically insulating coating on the apparatus likely to contact the patient. The inherent advantages and improvements of the present invention will become more readily apparent upon reference to the following detailed description of the invention and by reference to the drawings wherein:

FIG. 1 is a perspective view of the leg immobilizing apparatus of the present invention;

FIG. 2 is a fragmentary, exploded perspective view of the right end of the leg immobilizing apparatus of FIG. 1;

FIG. 3 is a front elevational view of the leg immobilizing apparatus of FIG. 1 taken partially in vertical cross section;

FIG. 4 is a top plan view of the leg immobilizing apparatus of FIG. 3;

DETAILED DESCRIPTION OF THE INVENTION

Figure 5:
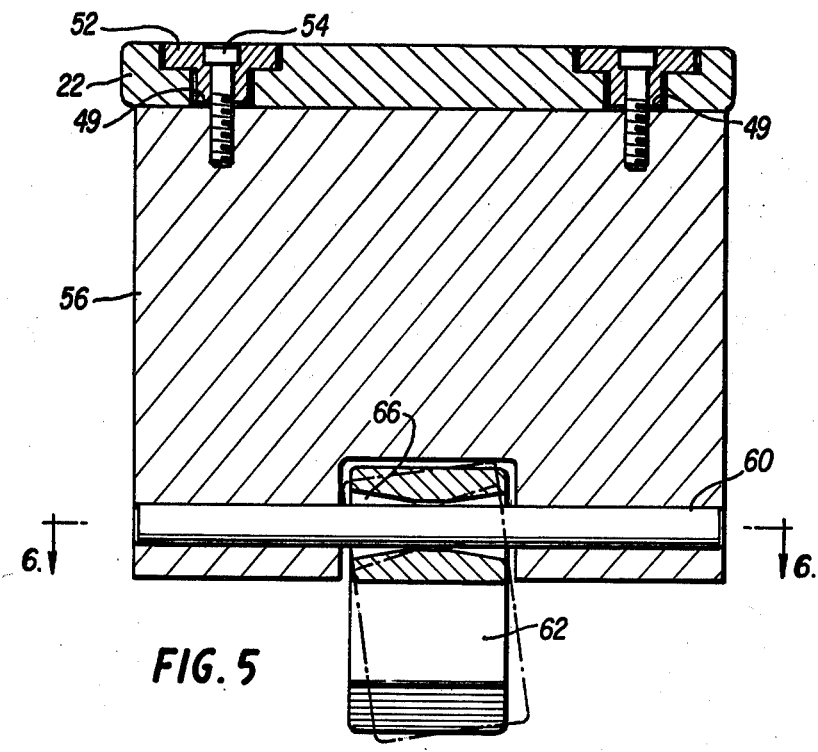
FIG. 5 is an elevational view taken in vertical cross section along line 5—5 of FIG. 4 and drawn to an enlarged scale.

Referring now to FIG. 1 of the drawings, there is illustrated a leg immobilizing apparatus indicated generally at 20. The leg immobilizing apparatus 20 has a bar member 22 which extends substantially entirely across the operating table and above a pair of horizontally extending parallel rail members indicated in phantom at 24. A pair of depending clamping means indicated generally at 26 are clamped to the rail members 24 in a manner described hereinafter.

The bar member 22 is provided with a pair of angularly disposed plate members 28 which as illustrated make approximately a 30 degree angle with respect to the bar member leaving an included angle between the plate members of 120 degrees. The angularity is not critical and may be varied as desired, since the purpose is to provide a cradling means for the leg of the patient to be operated upon. The plate member 28 are attached to the bar member 22 by means of suitable mounting brackets 30. These mounting brackets are selectively positioned in accordance with the size of the patient's thigh along the bar member 22 in apertures 32 and secured to the bar members by means of flush mounting bolts 33 as seen in cross section in FIG. 3.

The plate members 28 are provided with Velcro pads 34 which are bolted or screwed to the plate members 28 through mounting holes 36. Velcro is a trademark of Velcro, Inc., of Manchester, N.H., for separable fasteners, namely, hook and loop type fasteners.

A strap 38 which resembles a seat belt fastening means is provided with a buckle assembly indicated generally at 40 and has its ends 42 secured to the cradling means by providing the plate members 28 with slotted portions to receive the ends 42. The strap 38 may be provided with a pull handle 46 on one end thereof to secure the thigh of the patient in place.

Figure 6:
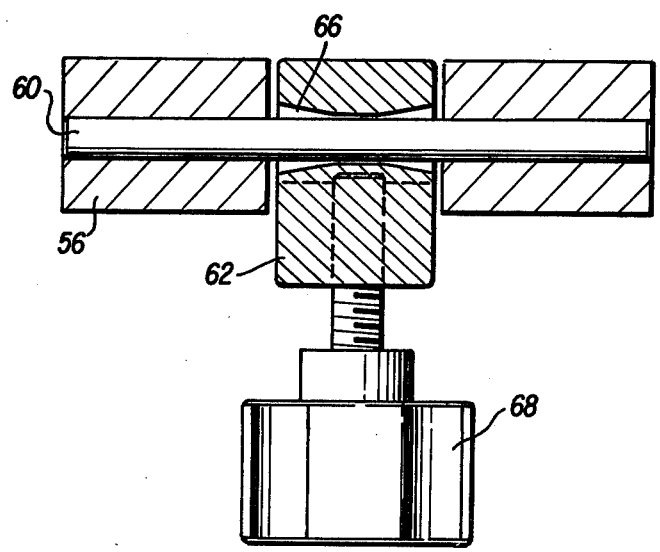
FIG. 6 is a plan view taken in horizontal cross section along line 6—6 of FIG. 5.

The left hand end of the bar member 22 in FIGS. 1 and 2 is shown to be provided with bolts 48 for attachment of a depending clamping means 26 while the right hand end of bar member 22 is shown to be slotted as seen best in FIG. 2 at 50 in order to receive a T-shaped bolt receptor member 52 for bolts 54. These bolts 54 extend through the T-shaped bolt receptors, then through shim members 49 into the upper surface of a clamp holder member 56 which is further provided with a centrally located notch-like opening 58. The clamp holder member 56 is also provided with apertures 59 to receive a mounting pin 60. Pin 60 supports a jaw member 62 of the clamping member with jaw member 62 being slotted at 64 to receive the parallel rails 24 of the operating table. The jaw member 62 as illustrated in FIGS. 5 and 6 is provided with a drilled and tapered aperture 66 so as to permit limited arcuate movement in a plane normal to the horizontally extending rail members 24 as well as limited arcuate movement in a plane coincident with the longitudinal axis of the horizontally extending rail members 24. This configuration also compensates for slightly different spacings between the horizontally extending rail members 24 of different operating tables. A bolt 68 secures the jaw member in its final position to the rail members 24.

Figure 7:
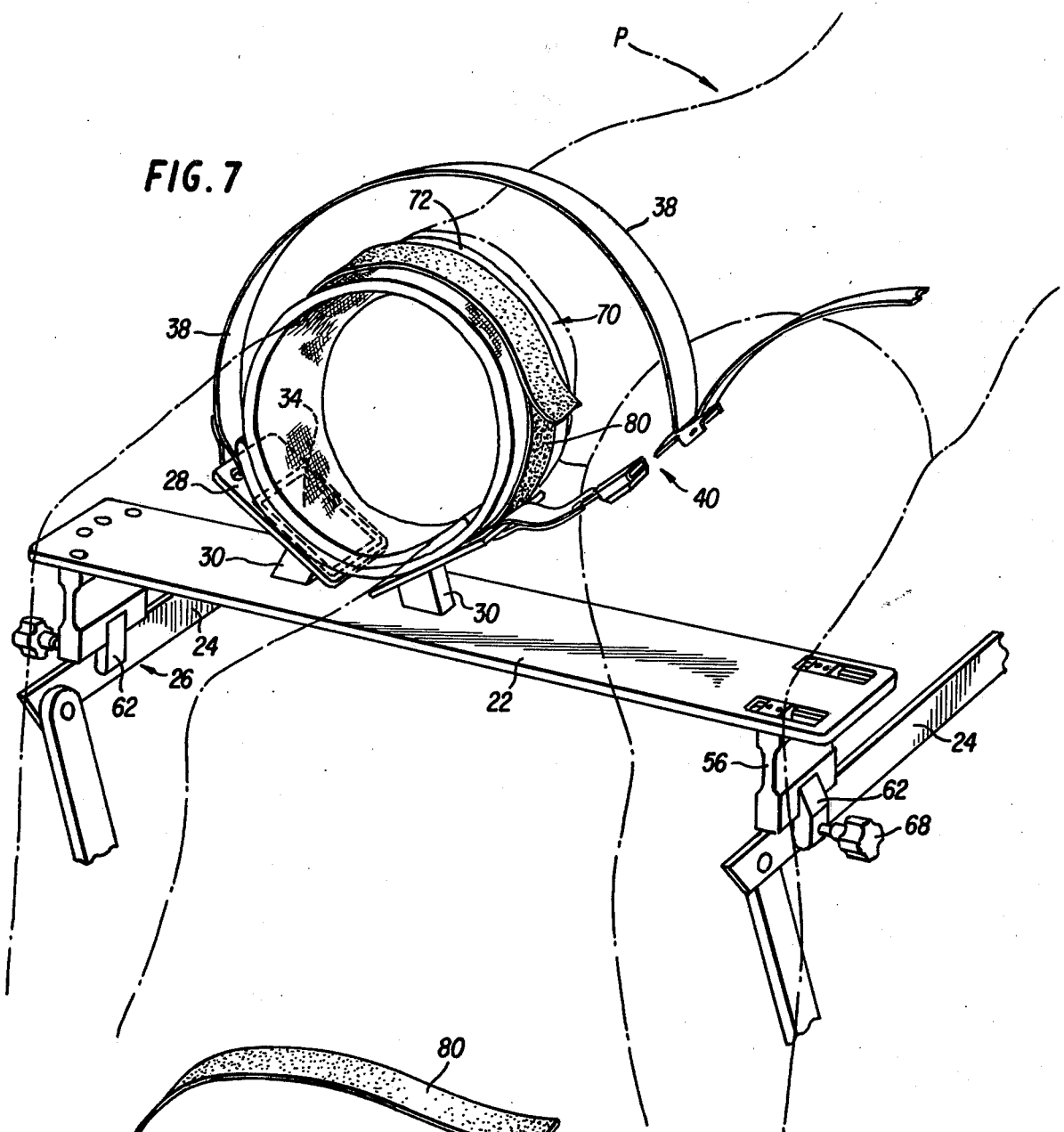
FIG. 7 is a perspective view of the leg immobilizing apparatus of FIG. 1 demonstrating its use.
Figure 8:
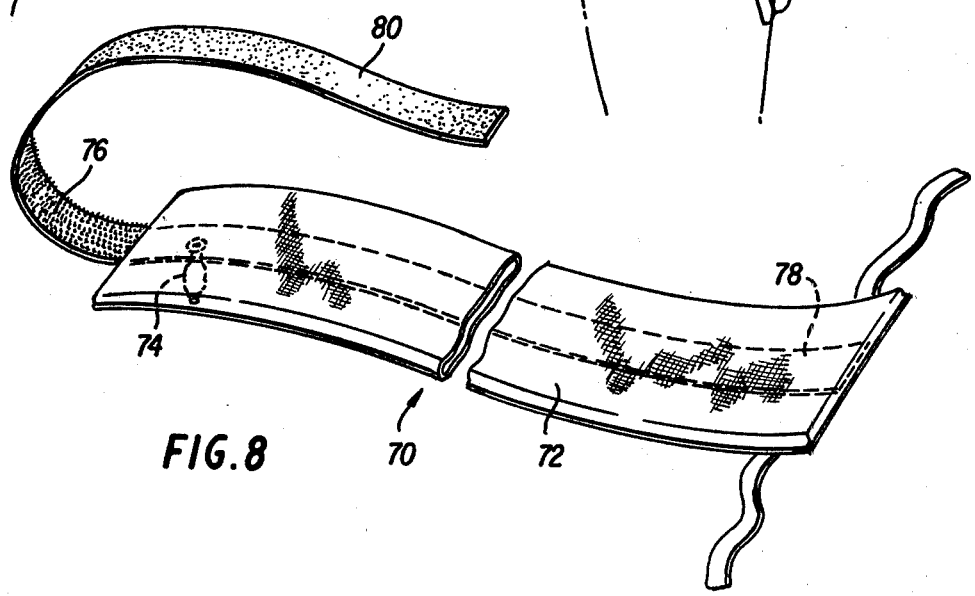
FIG. 8 is a fragmentary perspective view of a sphygmomanometer used in FIG. 7, drawn to an enlarged scale.
Figure 9:
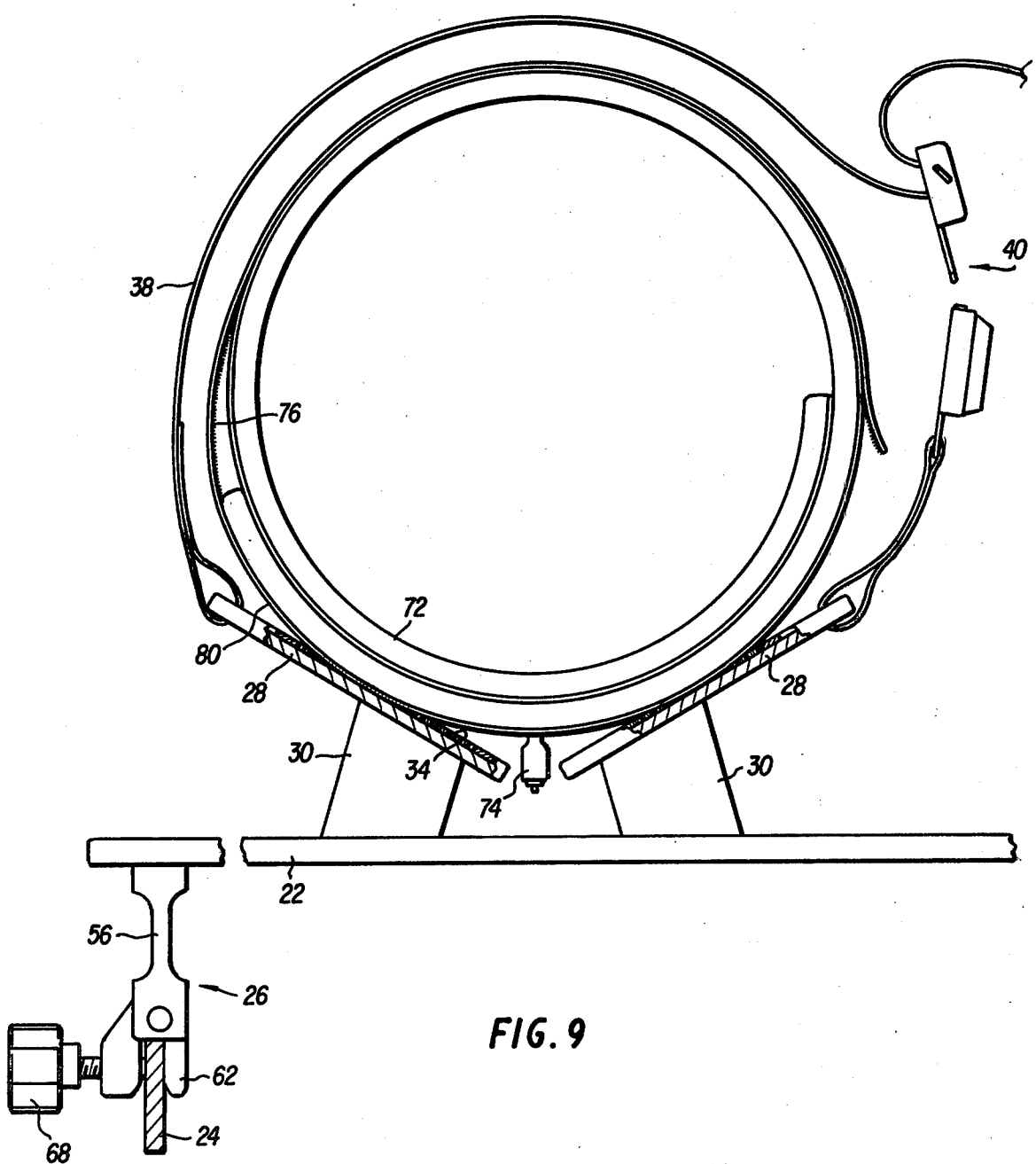
FIG. 9 is a fragmentary elevational view of the leg immobilizing apparatus of FIG. 7.

As is illustrated in FIGS. 7 and 8, the patient P is shown in FIG. 7 to have his right leg supported by the cradling means provided by the angularly positioned plate members 28. If the left knee of the patient P were to be operated upon, the bar member 22 would be turned end for end so that the cradling means provided by plate members 28 would be nearer the opposite side of the operating table. The patient P is shown to have the sphygmomanometer which constitutes tourniquet means 70 in place. As is illustrated in FIG. 8, this tourniquet means 70 includes a main body portion 72, a valve means 74 which is disposed downwardly between the two plate members 28, in a manner more fully illustrated in FIG. 9, with suitable pneumatic means (not shown) attached thereto which preferably extends through one of the apertures 33 between the plate members to apply the tourniquet to the thigh of the patient. This tourniquet means 70 not only includes Velcro at 76 which is attached to itself at 78, but also Velcro means 80 which is placed exteriorly of the strap and is attached to each of the Velcro plates 34 on the plate members 28 to secure the thigh and leg of the patient in proper position prior to pulling the strap 38 tightly by means of the hand pull means 46.

Figure 10:
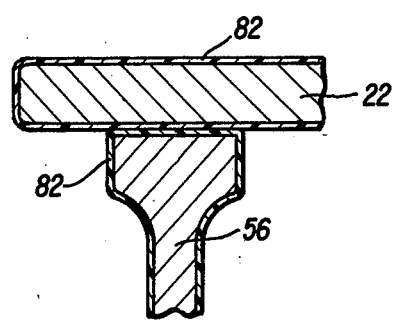
FIG. 10 is a fragmentary elevational view showing an end of the leg immobilizing apparatus with an electrically non-conducting coating and drawn to an enlarged scale.

FIG. 10 illustrates that it is preferred to provide an electrically insulating coating such as an anodized aluminum coating 82 to the bar member 22 and the clamp holder member 56 to prevent an electric shock to the patient. Customarily, the patient is electrically grounded.

In operation, the plate member is placed across the operating table with the cradling means provided by plate members 28 on the side of the table as illustrated in FIG. 7 for a right knee operation or with the bar member turned end for end to position the cradling means on the right side of the table for operation on the left knee. The tapered apertures 66 allow for misalignment at right angles to the rail members 24. Slots 50 and the T-shaped bolt receptors allow for varying widths between the rail members 24. Shims 49 can be removed and T-shaped receptors clamped permanently in place if variation in width is not needed. The bolt members 68 tighten the jaw members 62 to the respective rail members 24 and the tourniquet means 70 is draped over the plate members 28 in position to receive the thigh of the patient P. The tourniquet means is then wrapped around the thigh with securement between Velcro members 76 and 78 being effected as well as securement of the external Velcro means 80 to the pair of Velcro pads 34 on the plate members 28. The strap means 38 is then tightened with the aid of the buckle assembly 40 and the pull handle 46 on one end of strap 38. A desired and controllable pressure is then applied to the thigh of the patient by pneumatic pressure means supplied to valve means 74 of the tourniquet means 70.

A local anesthetic is frequently all that is required for the arthroscopic knee surgery of the present invention. The surgeon may then proceed with the operation relying upon the magnified image of the arthroscope on a television screen in the preferred embodiment.

Various changes and modifications may be made to the present apparatus. For example, the mounting for the plate members 28 may be made adjustable by means of a ball and socket arrangement permitting the thigh being operated upon to be elevated, if desired. Customarily, the leg of the patient which is not being operated upon is placed upon a pillow on the bar 22 and if desired, this pillow could also be secured to the bar member by further Velcro means. This pillow may also be used between the angle plates to provide comfort to the leg being operated on prior to the operation. The angle between the plate members 28 can be made adjustable. Coatings for the bar member 22 and the clamp holder member 56 may be other than an aluminum hardened coating. For example, a vinyl coating is possible just as long as the patient is electrically insulated from these members since electrical currents abound and saline is used to irrigate the knee during the operation. The jaw member 62 is preferably made of steel which is chrome plated.

While presently preferred embodiments of the invention have been illustrated and described, it will be recognized that the invention may be otherwise variously embodied and practiced within the scope of the claims which follow.

We claim:

1. A leg immobilizing apparatus for use in conjunction with an operating table, said operating table having a pair of horizontally extending rail means on opposite sides of said table, said apparatus comprising:
   a. bar means extendable entirely across said operating table, said bar means being provided with an electrically insulating coating,
   b. depending clamping means on said bar means adapted to be clamped to said horizontally extending rail means,
   c. cradling means on said bar means to cradle a leg of a patient,
   d. and tourniquet means for stopping the flow of blood in the patient's leg.

2. A leg immobilizing apparatus as defined in claim 1 including safety belt means with a quick release buckle anchored to said cradling means constituting a supplementary leg hold down means.

3. A leg immobilizing apparatus as defined in claim 1 including means for securing said tourniquet means to said cradling means.

4. A leg immobilizing apparatus as defined in claim 1 wherein said tourniquet means is secured both to itself and to said cradling means by Velcro.

5. A leg immobilizing apparatus as defined in claim 1 wherein said bar means includes slot means by means of which said depending clamping means may be secured in various positions to compensate for different lateral spacings between said horizontally extending rail means on different operating tables.

6. A leg immobilizing apparatus as defined in claim 1 wherein each depending clamping means has a rail engaging member provided with slot means to receive one of said horizontally extending rail means with said rail means being releasably retained therein.

7. A leg immobilizing apparatus as defined in claim 6 wherein said rail engaging member of each depending clamping means is pin mounted beneath said bar means so as to permit limited arcuate movement in a plane normal to said horizontally extending rail means and limited arcuate movement in a plane coincident with the longitudinal axis of said horizontally extending rail means.

8. A leg immobilizing apparatus as defined in claim 1 wherein said cradling means comprise a pair of plate members angularly mounted with respect to said bar means.

9. A leg immobilizing apparatus as defined in claim 8 wherein each plate member includes a receptor means secured to a plate member for attaching said tourniquet means thereto.

10. A leg immobilizing apparatus as defined in claim 9 wherein said receptor means carries a Velcro patch member engageable with a complementary strip thereof carried exteriorly of said tourniquet means.

11. A leg immobilizing apparatus as defined in claim 8 including safety belt means with a quick release buckle anchored to said plate members constituting a supplementary leg hold down means.

12. A leg immobilizing apparatus as defined in claim 3 including safety belt means with a quick release buckle anchored to said cradling means constituting a supplementary leg hold down means.

13. A leg immobilizing apparatus as defined in claim 3 wherein said tourniquet means is secured both to itself and to said cradling means by Velcro.

14. A leg immobilizing apparatus as defined in claim 3 wherein said bar means includes slot means by means of which said depending clamping means may be secured in various positions to compensate for different lateral spacings between said horizontally extending rail means on different operating tables.

15. A leg immobilizing apparatus as defined in claim 3 wherein each depending clamping means has a rail engaging member provided with slot means to receive one of said horizontally extending rail means with said rail means being releasably retained therein.

16. A leg immobilizing apparatus as defined in claim 15 wherein said rial engaging member of each depending clamping means is pin mounted beneath said bar means so as to permit limited arcuate movement in a plane normal to said horizontally extending rail means and limited arcuate movement in a plane coincident with the longitudinal axis of said horizontally extending rail means.

17. A leg immobilizing apparatus as defined in claim 3 wherein said cradling means comprise a pair of plate members angularly mounted with respect to said bar means.

18. A leg immobilizing apparatus as defined in claim 5 where said slot means includes a bolt receptor member received in said bar means and shim means between said bolt receptor member and said clamping means.

19. A leg immobilizing apparatus as defined in claim 17 wherein each plate member includes a receptor means secured to a plate member for attaching said tourniquet means thereto.

20. A leg immobilizing apparatus as defined in claim 19 wherein said receptor means carries a Velcro patch member engageable with a complementary strip thereof carried exteriorly of said tourniquet means.

21. A leg immobilizing apparatus as defined in claim 17 including safety belt means with a quick release buckle anchored to said plate members constituting a supplementary leg hold down means.

22. A leg immobilizing apparatus as defined in claim 14 wherein said slot means includes a bolt receptor member received in said bar means and ship means between said bolt receptor member and said clamping means.

* * * * *